(12) United States Patent
Bonde (10) Patent No.: US 8,694,125 B2
(45) Date of Patent: Apr. 8, 2014

(54) MEDICAL LEADS HAVING A DISTAL BODY AND AN OPENLY COILED FILAR

(71) Applicant: Medtronic, Inc., Minneapolis, MN (US)

(72) Inventor: Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/752,587

(22) Filed: Jan. 29, 2013

(65) Prior Publication Data

US 2013/0282089 A1 Oct. 24, 2013

Related U.S. Application Data

(60) Provisional application No. 61/635,808, filed on Apr. 19, 2012.

(51) Int. Cl.
*A61N 1/00* (2006.01)
(52) U.S. Cl.
USPC ........................................................ 607/116
(58) Field of Classification Search
USPC ........................................................ 607/116
See application file for complete search history.

(56) References Cited

U.S. PATENT DOCUMENTS

| | | | |
|---|---|---|---|
| 5,571,157 A | 11/1996 | McConnell | |
| 6,240,322 B1 | 5/2001 | Peterfeso et al. | |
| 8,036,756 B2 | 10/2011 | Swoyer et al. | |
| 2006/0015164 A1* | 1/2006 | Partridge et al. | 607/119 |
| 2010/0268310 A1 | 10/2010 | Bonde et al. | |

\* cited by examiner

*Primary Examiner* — Robert N Wieland (57) ABSTRACT

Medical leads have one or more openly coiled filars and a distal body coupled to the openly coiled filars. The openly coiled filars provide a lead with compliance and elasticity while the distal body provides the firmness needed for placement and support of the electrodes. The openly coiled filars transition to a linear distal portion that extends to the distal body, and the distal body has proximal tines that fold proximally to a collapsed state. The linear distal portions of the filars pass through the tines when entering the distal body. Placing tension on the linear distal portions causes the tines to be rotated proximally to the collapsed state. Such tension may be created by a stylet pressing distally against the distal body during implantation. Such tension may also be created by applying a force in the proximal direction to the coiled filars during explantation.

14 Claims, 7 Drawing Sheets

MEDICAL LEADS HAVING A DISTAL BODY AND AN OPENLY COILED FILAR

TECHNICAL FIELD

Embodiments are related to medical leads that carry stimulation signals. More particularly, embodiments are related to medical leads that have a distal body and openly coiled filars.

BACKGROUND

Medical leads are used in conjunction with a medical device that generates stimulation signals to deliver the stimulation signals from the medical device to a target stimulation site within a body of a patient. The medical leads may be implanted through a percutaneous procedure where an introducer needle is inserted into the body, and a medical lead is inserted through a lumen in the needle. A stylet may be included within a lumen of the medical lead to guide the medical lead from the needle to the target site.

One issue when implanting the medical lead is that the needle must be of adequate size to facilitate the introduction of the medical lead. However, a smaller needle is less bothersome to the patient. Thus, minimizing the diameter of the lead is desirable so that the size of the introducer needle may also be minimized.

Another issue that occurs once the medical lead is implanted is that the medical lead needs to have a fixed position at the target site, which is particularly true when assessing the efficacy of therapy during a trial period. Movements by the patient may encourage the medical lead to migrate and therefore a fixation structure may be required to provide the fixation of the lead at the target site. However, the structure for fixation may contribute to the size of the medical lead which may call for an undesirable increase in the size of the introducer needle. Furthermore, explantation of the lead may be more difficult due to the presence of the fixation structure which resists movement in the direction of explantation.

The effectiveness of a fixation structure may also be limited by the compliance of the body of the lead. The body of the lead needs a degree of firmness to support the electrodes and to maintain their alignment when at the target site. Yet a stiff lead body extending toward the proximal end of the lead is counterproductive to the fixation structure.

SUMMARY

Embodiments address issues such as these and others by providing a body that utilizes one or more openly coiled filars that act as a portion of the lead body and provides a relatively high degree of compliance. A distal body is present at the distal end of the one or more coiled filars where the distal body provides a firmer support for the electrodes. The distal body includes one or more tines on the proximal end that offer fixation. The coiled filar(s) have a linear distal end including a proximal portion of the linear distal end that is proximal of the distal body and tines and have a distal portion of the linear distal end that passes through the tines and the distal body. The one or more tines may collapse in the proximal direction to avoid increasing the diameter of the lead. Applying a proximal force on the coiled filar(s) such as when explanting the medical lead causes the linear distal end of the filar(s) to force the tine(s) into the collapsed state.

Embodiments further provide a medical lead that includes an openly coiled filar that has a linear distal end. The medical lead includes a distal body having an electrode and also having a first tine on a proximal end, with a distal portion of the linear distal end of the coiled filar passing through the distal body and first tine and being coupled to the electrode. A junction of the at least one tine to the distal body provides a hinge point, the first tine being rotatable about the hinge point between a collapsed state and an extended state. The first tine rotates in the proximal direction from the extended state to the collapsed state.

Embodiments provide a medical system that includes a stimulation device and a medical lead with a proximal end coupled to the stimulation device. The medical lead includes an openly coiled filar that has a linear distal end. The medical lead includes a distal body having an electrode and also having a first tine on a proximal end, with a distal portion of the linear distal end of the coiled filar passing through the distal body and first tine and being coupled to the electrode. A junction of the at least one tine to the distal body provides a hinge point, the first tine being rotatable about the hinge point between a collapsed state and an extended state. The first tine rotates in the proximal direction from the extended state to the collapsed state.

Embodiments provide a method of positioning a medical lead that involves providing the medical lead having an openly coiled filar that has a linear distal end. The medical lead includes a distal body having an electrode and also having a first tine on a proximal end, with a distal portion of the linear distal end of the coiled filar passing through the distal body and first tine and being coupled to the electrode. A junction of the at least one tine to the distal body provides a hinge point, the first tine being rotatable about the hinge point between a collapsed state and an extended state. The first tine rotates in the proximal direction from the extended state to the collapsed state. The method further involves implanting the medical lead by routing the medical lead through a needle with the first tine in the collapsed state and with the first tine achieving the extended state upon exiting the needle and reaching the target site. The method also involves explanting the medical lead by applying force to the coiled filar in the proximal direction such that the distal portion of the linear distal end of the coiled filar within the first tine forces the first tine to rotate proximally to the collapsed state.

DETAILED DESCRIPTION

Embodiments of medical leads include a compliant lead body formed by one or more openly coiled filars with a firmer distal body coupled to distal ends of the one or more filars. The distal body supports the electrodes and includes proximal tines that collapse in the proximal direction to minimize the distal body diameter. The distal ends of the coiled airs pass through the tines such that applying a proximal force to the filars causes the tines to be rotated proximally to the collapsed state.

Figure 1:
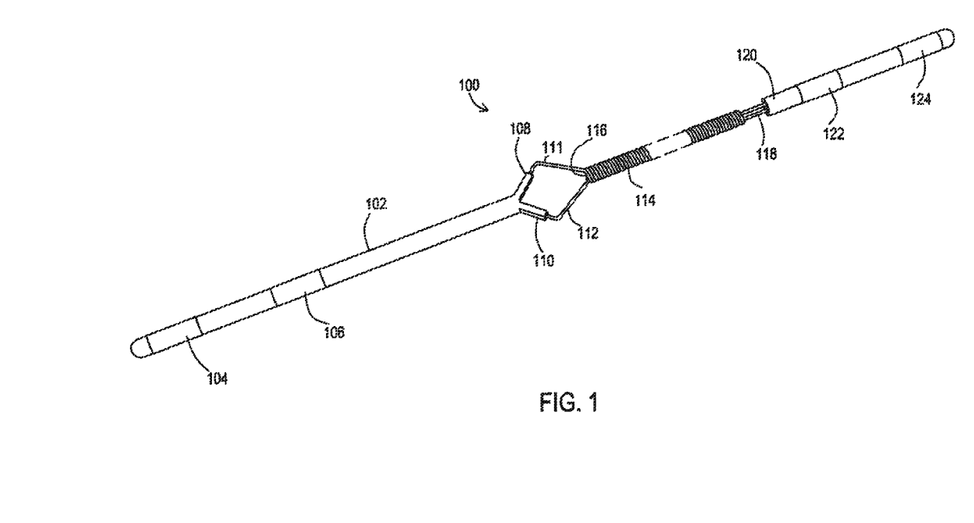
FIG. 1 shows an example of a medical lead according to various embodiments.
Figure 2:
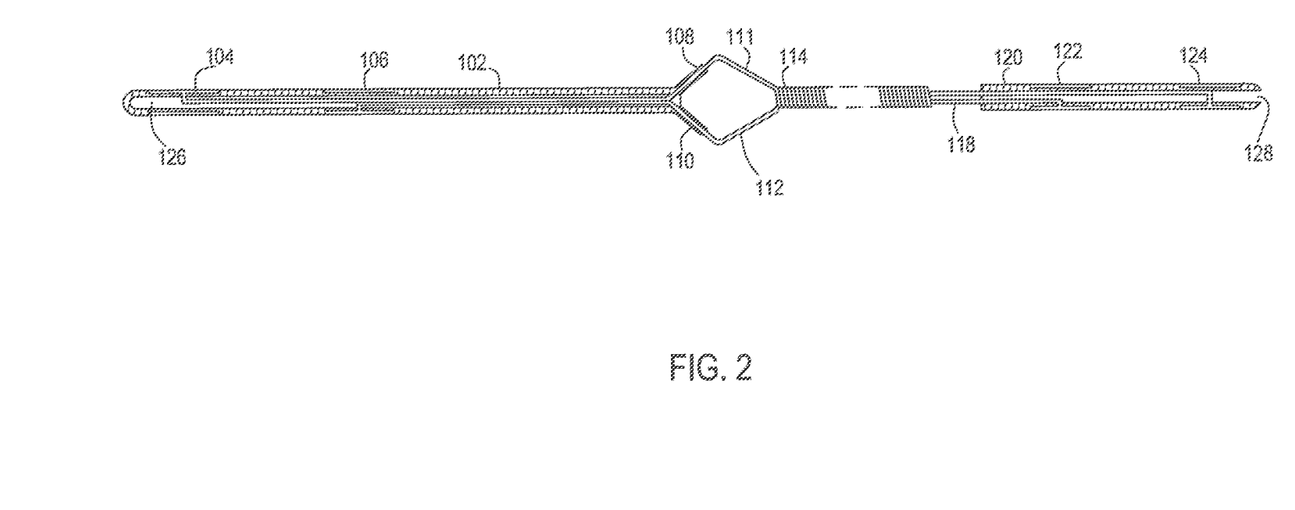
FIG. 2 shows a longitudinal cross-section of the medical lead of FIG. 1.

FIGS. 1 and 2 show one example of a medical lead 100 having a central portion 114 of a filar that is openly coiled. In other words, the coiled filar is not surrounded by a protective tubular jacket but is instead itself the lead body. This openly coiled filar portion 114 provides a relatively high degree of compliance and elasticity for the lead 100. The filar may be constructed of various biocompatible conductors such as stainless steel alloys (316L, 316LVM, MP35N, etc.) or other biocompatible metals and alloys of platinum such as (Pt—Ir) or alloys of titanium such as (TiOsteum® or Ti-15Mo) that have a non-conductive coating such as polyethylene-co-tetrafluoroethylene (ETFE), polytetrafluoroethylene (PTFE or Teflon®), polyurethanes, polyimides, etc. The coiled shape defines a lumen 116 through which a stylet may be passed when implanting the medical lead 100.

In this particular example, both a proximal filar portion 118 and distal filar portions 112, 111 are linear rather than coiled. These linear portions 111,112 and 118 enter into respective distal and proximal bodies 102 and 120. It will be appreciated that the proximal portion 118 may be coiled as well.

The proximal body 120 of FIGS. 1 and 2 provides a firmer support for one or more contacts 122, 124 that are ultimately connected to a stimulation device. The proximal body 120 may be inserted into a bore within a stimulation device where the electrical connections occur. The proximal body 120 may be constructed of various nonconductive biocompatible materials such as polyurethane, polyether block amide (PEBA or PEBAX®), polyether ether ketone or polyaryletherketone (PEEK) for example as well as others. The proximal body 120 may define a lumen 128 that allows a stylet to be inserted during implantation of the medical lead 100.

The proximal portion 118 of the filar(s) may extend through the proximal body 120 until reaching the respective contacts 122, 124. The proximal portion 118 of the filar(s) is then physically and electrically coupled to the respective contacts 122, 124.

The distal body 102 provides a firmer support for one or more electrodes 104, 106 that are ultimately positioned at the target stimulation site within the body of the patient. The distal body 102 may be constructed of various nonconductive biocompatible materials such as polyurethane, silicone, and surface-modified endgroup (SME) polyurethanes to provide such firmness. The distal body 102 may define a lumen 126 that allows a stylet to be inserted when implanting the medical lead 100.

The distal portions 111, 112 of the filar(s) may extend through the distal body 102 until then coupling to the respective electrode 104, 106. The filars may be present within the lumen 126 or may otherwise tunnel through the distal body 102 until reaching the electrode 104, 106. Furthermore, the distal-most region of the distal filar portions 111, 112 which is present within the lumen 126 may be coiled rather than linear, which provides an additional mechanical advantage during explantation to minimize strain on the bond of the filars 111, 112 to the electrodes 104, 106. Another manner of minimizing such strain during explantation involves using a polyurethane coating directly on the metal of the filars 111, 112 and then allowing the polyurethane coating to achieve a bond with the polymer forming the distal body 102.

To provide fixation for the electrodes 104, 106, the distal body 102 further defines one or more proximal tines 108, 110. As shown in FIGS. 1 and 2, two tines 108, 110 are present on opposite sides of the proximal end of the distal body 102 but any number of tines may be present in various embodiments. These tines 108, 110 have a natural extended state as shown in FIGS. 1 and 2 whereby the tines 108, 110 extend from the distal body 102 at a particular angle. In this extended state, the tines 108, 110 effectively catch upon the surrounding tissue of the body to resist movement in the proximal and distal directions. The amount of fixation force created by the tines 108, 110 can be controlled by the physical dimensions chosen fir the tines 108, 110 including the angle, the length, the width, the thickness, and the geometry. Thus, the medical lead 100 may be selected for a particular implantation scenario based on having a tine design that meets the fixation requirements of the scenario.

The distal body 102 and tines 108, 110 may be constructed by being molded onto the linear distal end 112 of the filars, with the filars passing through the tines 108, 110. An alternative construction would be to pre-construct the tines 108, 110 with lumens therein and feed the linear distal ends of the filars through the lumens of the tines 108, 110. Then the distal body 102 may be molded onto the linear distal ends with the tines 108, 110 reflowing to create the junction with the proximal end of the distal body 102. Another alternative construction would be to use basic polyurethane tubing and thermally form the tines with the polyurethane tubing while at the same time bonding to the distal tubing.

During implantation, the tines 108, 110 can be forced into a collapsed state where the tines 108, 110 are rotated proximally about a hinge point that occurs at the junction of the tines 108, 110 to the distal body 102 by insertion in the distal direction into a lumen of an introducer needle and/or by application of tension from applying force in the distal direction by a stylet pressing against the distal body 102. Once fully rotated, the tines 108, 110 become adjacent to the linear distal portion 112 of the filar(s) so that the overall diameter of the medical lead is no greater than the diameter of the distal body 102. Therefore, the presence of the tines 108, 110 does not require an increase in size of the lumen of the introducer needle.

During explantation, the tines 108, 110 can be forced back to the collapsed state by the tines 108, 110 rotating proximally. The extraction force applied to the coil 114 or proximal section 118 in the proximal direction effectively puts tension on the linear distal portions 111, 112. This tension on distal portions 111, 112 overcomes the natural reluctance of the tines 108, 110 to rotate proximally from the extended state back to the collapsed state and thereby forces such proximal rotation of the tines 108, 110 to the collapsed state.

Figure 3:
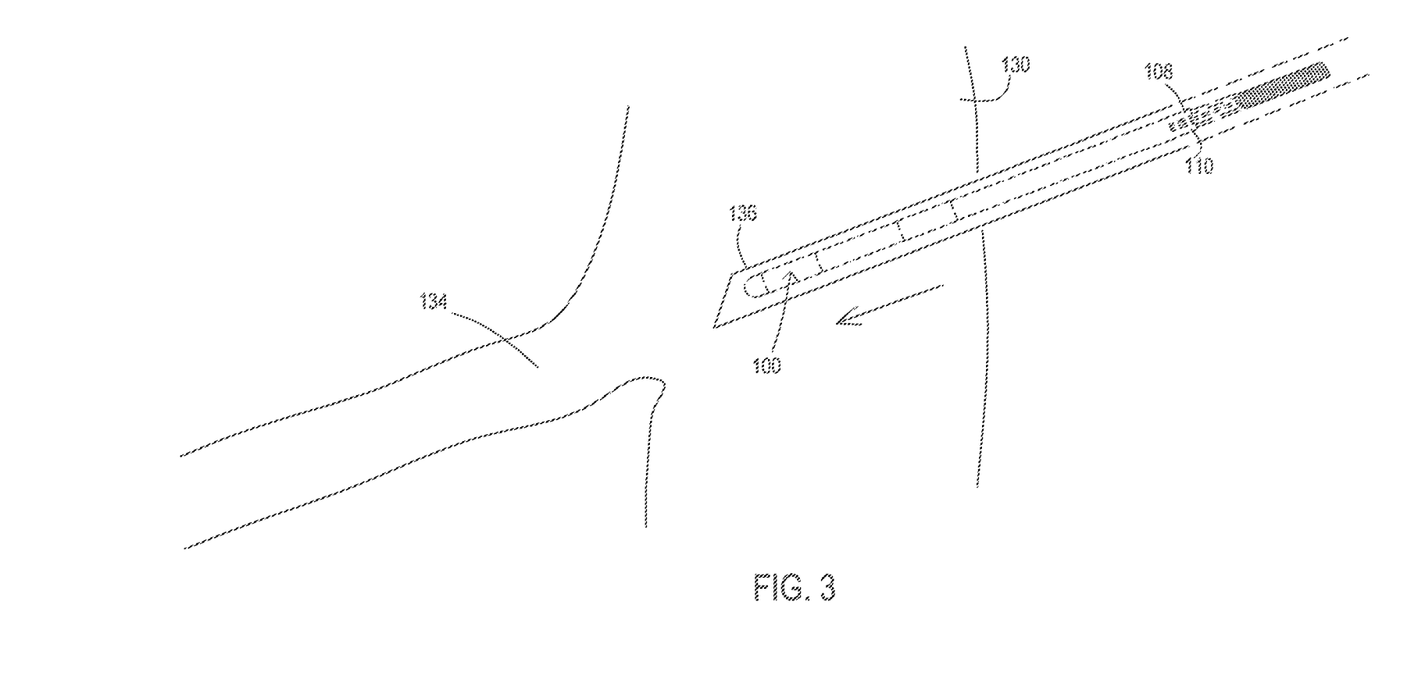
FIG. 3 shows a first stage of one example of an implantation procedure of the medical lead of FIG. 1.
Figure 4:
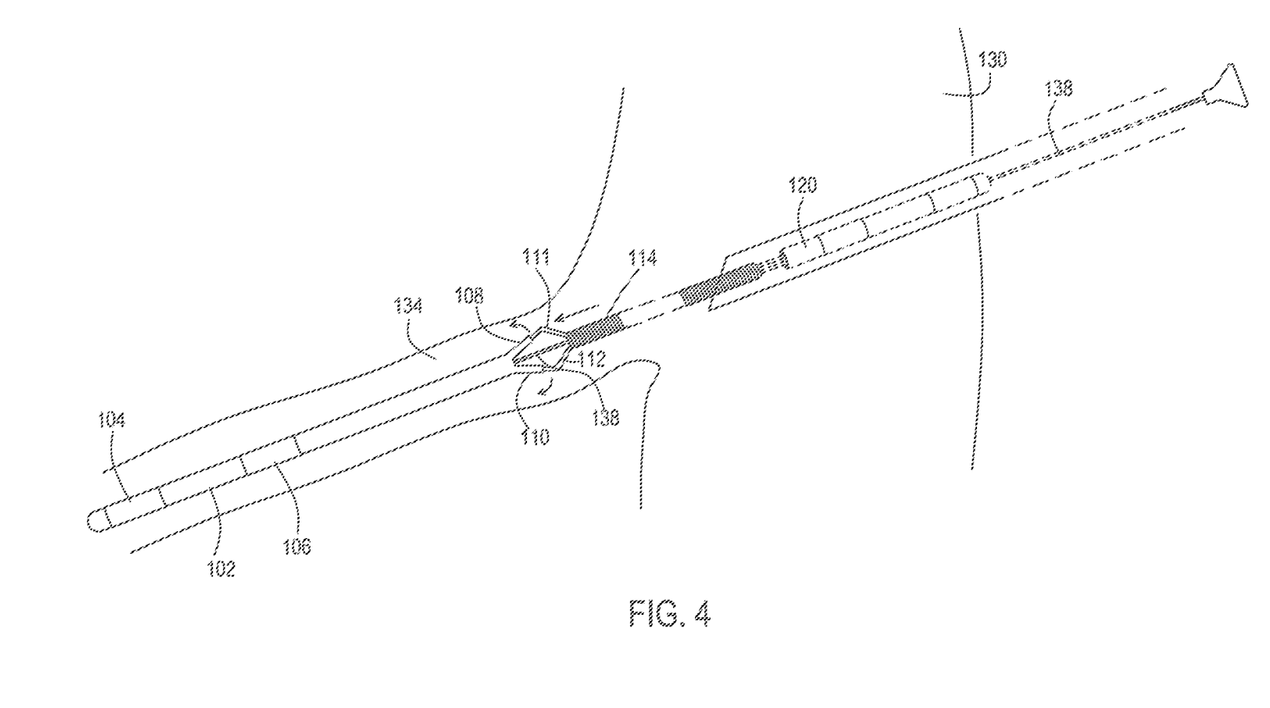
FIG. 4 shows a second stage of the implantation procedure.
Figure 5:
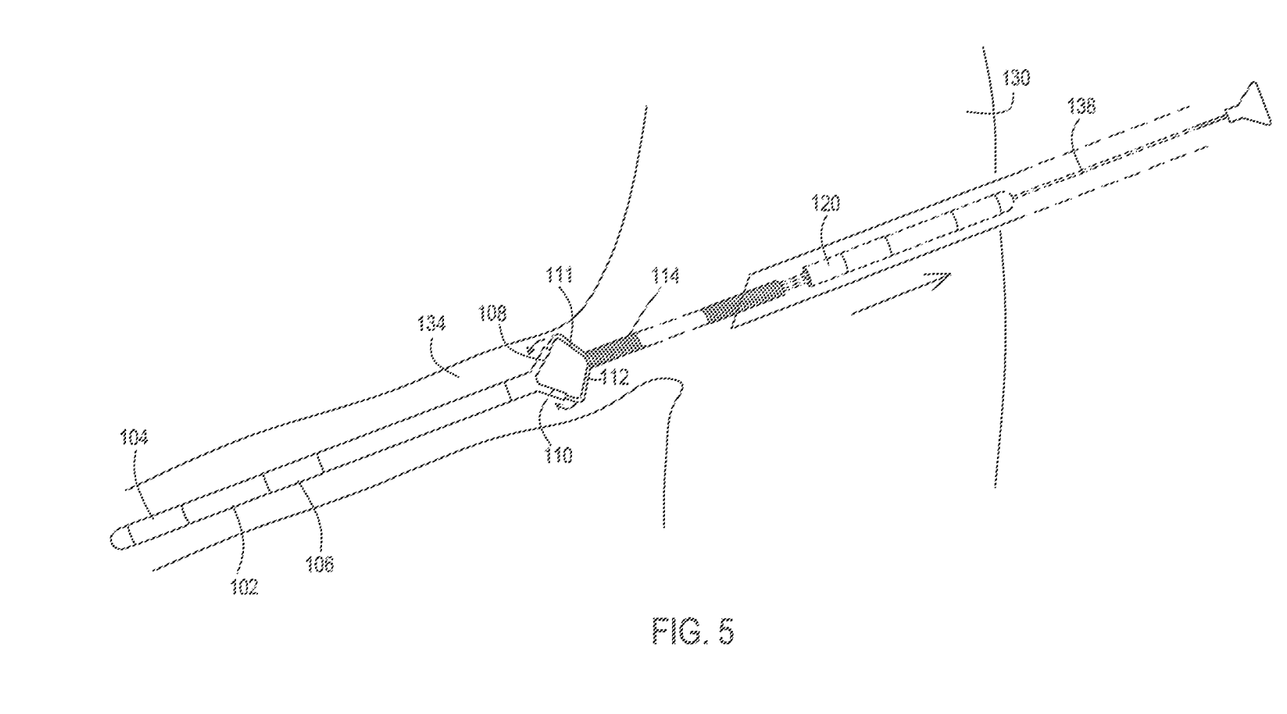
FIG. 5 shows a third stage of the implantation procedure.

One example of the process of implantation is shown in FIGS. 3-5. In FIG. 3, the medical lead of FIG. 1 is located within a lumen of the introducer needle 136, and the tines 108, 110 are in the proximally collapsed state. The introducer needle 136 is inserted through the body 130 of the patient and directed toward a target stimulation site. In this particular example, the target stimulation site is in close proximity to the sacrum in order to stimulate nearby the sacral nerve. For instance, the electrodes 104, 106 may be positioned within a foramen 134 of the sacrum such that the needle 136 is directed to the foramen 134.

In this particular example, once the needle 136 has aligned with the foramen 134, the medical lead 100 is advanced distally from the needle 136 and through the foramen 134 by manipulation of a stylet 138 that is present within the lumens 116, 126, and 128 of the medical lead 100. The stylet 138 is used to steer the distal body 102 to the desired location relative to the sacral nerve.

As shown in FIG. 4, upon the distal body 102 exiting the needle 136 due to the force in the distal direction from the stylet against the distal body 102, the tines 108, 110 remain in the collapsed state due to the distal force from the stylet 138 maintain tension on the linear distal regions 111, 112.

As shown in FIG. 5, upon reaching the target site, the needle 136 and style 138 are then removed. This also removes the tension on the linear distal regions 111, 112 such that the tines 108, 110 then rotate distally to their natural extended position.

Figure 6:
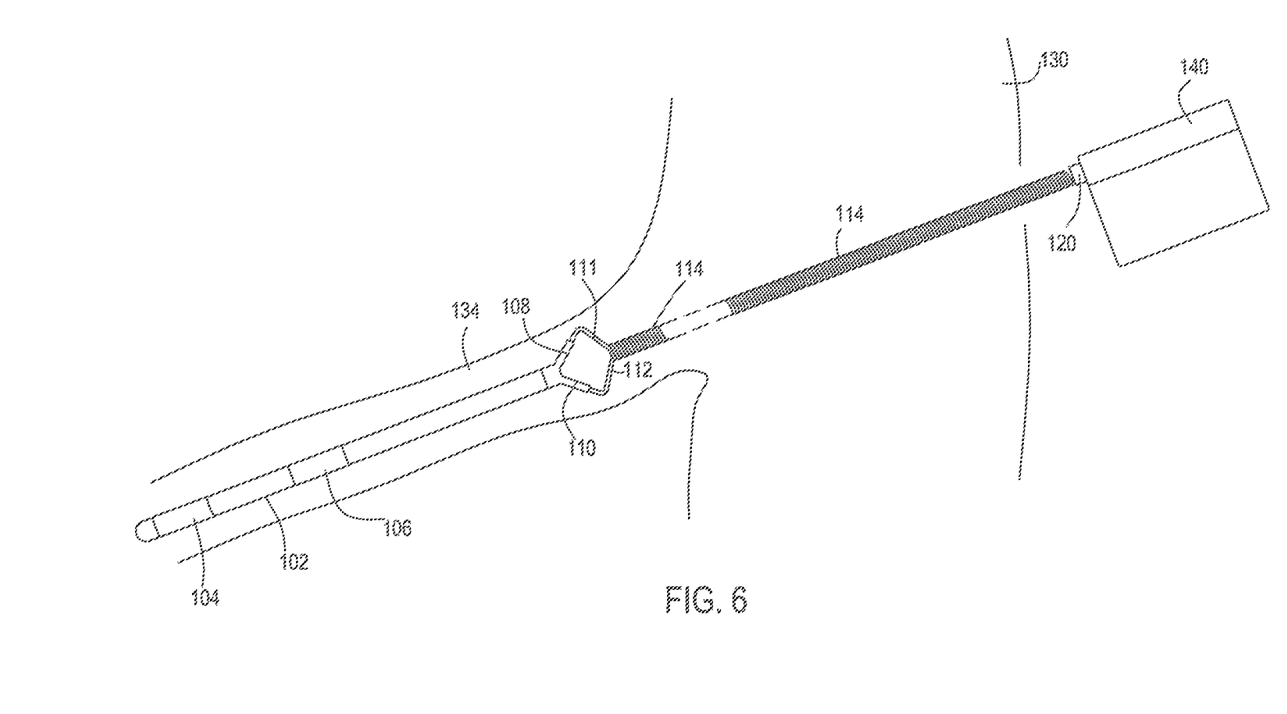
FIG. 6 shows the medical lead once implanted and connected to a stimulation device.

FIG. 6 shows the medical lead 100 with the distal body 102 in the target site with the electrodes 104, 106 being in proximity to the sacral nerve. The tines 108, 110 are in their fully extended state and provide maximum resistance to further movements of the distal body 102. The openly coiled filar portion 114 extends proximally back to a location where a stimulation device 140 is being positioned with the proximal body 120 being coupled to the stimulation device 140. In this example, the stimulation device 140 is a trial stimulation device being positioned externally on the body 130 such that the filar portion 114 extends beyond the outer surface of the body 130. However, it will be appreciated that in other examples the stimulation device 140 may be implanted within a pocket formed within the body 130.

Figure 7:
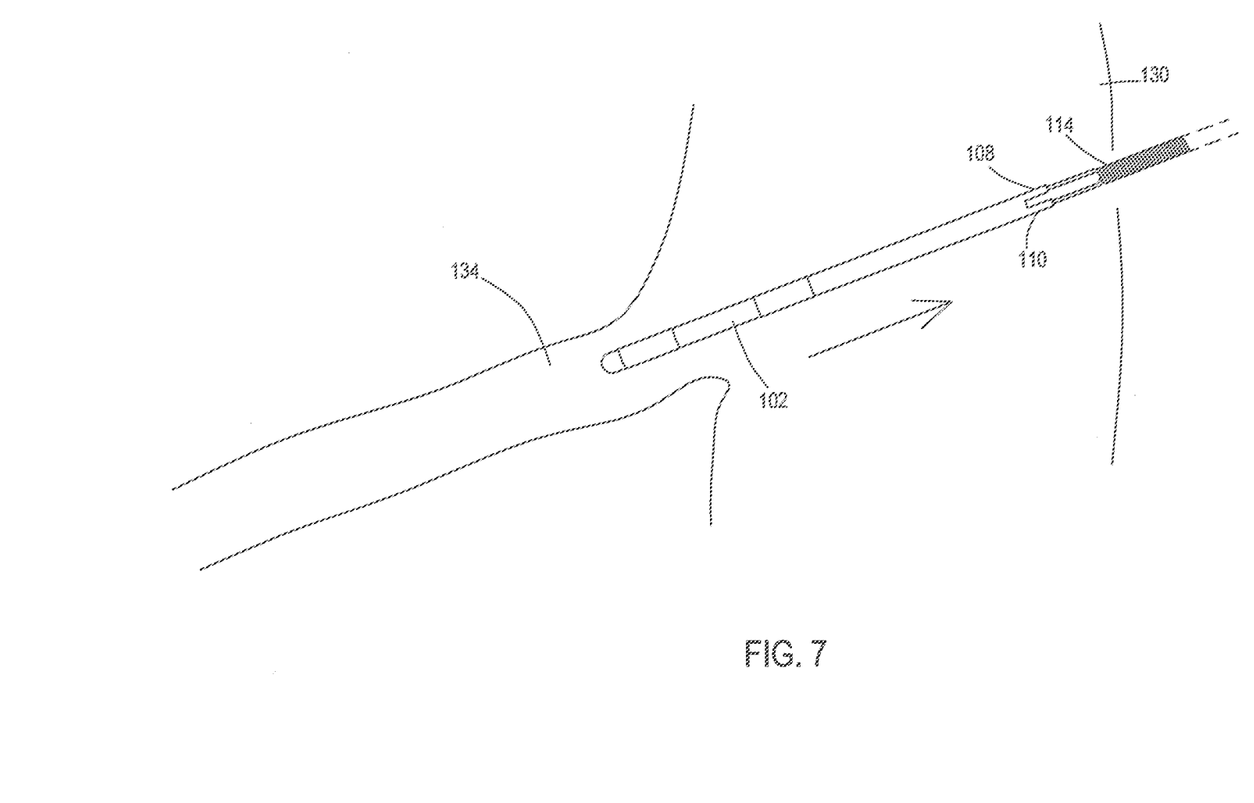
FIG. 7 shows an example of an explantation of the medical lead.

It may be desirable to subsequently explant the medical lead 100. This is particularly the case where the medical lead 100 has been implanted for a stimulation trial. This explantation of the medical lead 100 is shown in FIG. 7. In this case, a removal force is applied in the proximal direction to the proximal body 120 and the proximal end of the filar portion 114. This proximal force causes tension on the linear distal portions 111, 112 which causes the tines 108, 110 to rotate proximally until achieving the collapsed state as shown. The distal body 102 then proceeds proximally until exiting the body 130.

While embodiments have been particularly shown and described, it will be understood by those skilled in the art that various other changes in the form and details may be made therein without departing from the spirit and scope of the invention.

What is claimed is:

1. A medical lead, comprising:
an openly coiled filar that has a linear distal end;
a distal body having an electrode and also having a first tine on a proximal end, with a distal portion of the linear distal end of the coiled filar passing through the first tine and through the distal body and being coupled to the electrode, a junction of the at least one tine to the distal body providing a hinge point, the first tine being rotatable about the hinge point between a collapsed state and an extended state, the first tine rotating in the proximal direction from the extended state to the collapsed state.

2. The medical lead of claim 1, further comprising a proximal body separated from the distal body and having a contact, with a proximal end of the coiled filar passing through the proximal body and being coupled to the contact.

3. The medical lead of claim 1, wherein the distal body and the first tine are molded onto the linear distal end of the coiled filar with the linear distal end passing through the first tine.

4. The medical lead of claim 1, further comprising a second openly coiled filar paired with the openly coiled filar, the second openly coiled filar having a linear distal end and the distal body having a second tine and a second electrode, and wherein a distal portion of the linear distal end of the second coiled filar passes through the second tine and is coupled to the second electrode.

5. The medical lead of claim 4, wherein the first tine and the second tine are positioned on opposite sides of the distal body.

6. A medical system, comprising:
a stimulation device; and
a medical lead with a proximal end coupled to the stimulation device, the medical lead comprising:
an openly coiled filar that has a linear distal end; and
a distal body having an electrode and also having a first tine on a proximal end, with a distal portion of the linear distal end of the coiled filar passing through the first tine and through the distal body and being coupled to the electrode, a junction of the at least one tine to the distal body providing a hinge point, the first tine being rotatable about the hinge point between a collapsed state and an extended state, the first tine rotating in the proximal direction from the extended state to the collapsed state.

7. The medical system of claim 6, wherein the medical lead further comprises a proximal body separated from the distal body and having a contact, with a proximal end of the coiled filar passing through the proximal body and being coupled to the contact.

8. The medical system of claim 6, wherein the distal body and the first tine are molded onto the linear distal end of the coiled filar with the linear distal end passing through the first tine.

9. The medical system of claim 6, wherein the medical lead further comprises a second openly coiled filar paired with the openly coiled filar, the second openly coiled filar having a linear distal end and the distal body having a second tine and a second electrode, and wherein a distal portion of the linear distal end of the second coiled filar passes through the second tine and is coupled to the second electrode.

10. The medical system of claim 9, wherein the first tine and the second tine are positioned on opposite sides of the distal body.

11. A method of positioning a medical lead, comprising:
providing the medical lead having an openly coiled filar that has a linear distal end, the medical lead also having a distal body having an electrode and also having a first tine on a proximal end, with a distal portion of the linear distal end of the coiled filar passing through the first tine and the distal body and being coupled to the electrode, a junction point of the at least one tine to the distal body providing a hinge point, the first tine being rotatable about the hinge point between a collapsed state and an extended state, the first tine rotating in the proximal direction from the extended state to the collapsed state;
implanting the medical lead by routing the medical lead through a needle with the first tine in the collapsed state with the first tine achieving the extended state after exiting the needle and reaching a target site; and
explanting the medical lead by applying force to the coiled filar in the proximal direction such that the distal portion of the linear distal end of the coiled filar within the first tine forces the first tine to rotate proximally to the collapsed state.

12. The method of claim 11, wherein the medical lead has a second openly coiled filar paired with the openly coiled filar, the second openly coiled filar having a linear distal end and the distal body having a second tine and a second electrode, and wherein a distal portion of the linear distal end of the second coiled filar passes through the second tine and is coupled to the second electrode, and wherein explanting the medical lead further comprises applying force to the second coiled filar in the proximal direction such that the distal portion of the linear distal end of the second coiled filar within the second tine forces the second tine to rotate proximally to the collapsed state.

13. The method of claim 12, wherein the first tine and the second tine are positioned on opposite sides of the distal body.

14. The method of claim 12, wherein explanting the medical lead further comprises applying force to the coiled filar in the proximal direction simultaneously with applying force to the second coiled filar in the proximal direction.

\* \* \* \* \*